United States Patent [19]

Luck et al.

[11] Patent Number: 4,741,204

[45] Date of Patent: May 3, 1988

[54] MEASUREMENT OF THE DEPLETION OF BASIC ADDITIVES IN LUBRICATING OIL

[75] Inventors: Russell M. Luck, Monroeville; Allan I. Bennett, Murrysville, both of Pa.; David H. Taylor, Bloomington, Minn.

[73] Assignee: Thermo King Corporation, Minneapolis, Minn.

[21] Appl. No.: 39,145

[22] Filed: Apr. 16, 1987

[51] Int. Cl.⁴ .......................................... G01M 15/00
[52] U.S. Cl. .......................................... 73/116; 73/64; 436/61
[58] Field of Search ............... 73/10, 64, 116; 340/59; 338/27, 28; 436/61, 149; 324/65 CR

[56] References Cited

U.S. PATENT DOCUMENTS

| | | |
|---|---|---|
| 2,554,225 | 5/1951 | Taylor .................................. 73/1 R |
| 2,735,754 | 2/1956 | Dravnieks . |
| 2,851,570 | 9/1958 | Schaschl . |
| 2,987,685 | 6/1961 | Schaschl . |
| 2,991,439 | 7/1961 | Marsh et al. . |
| 2,994,219 | 8/1961 | Schaschl . |
| 3,004,232 | 10/1961 | Schaschl et al. . |
| 3,060,721 | 10/1962 | Marsh et al. . |
| 3,073,154 | 1/1963 | Schaschl et al. . |
| 3,108,242 | 10/1963 | Scott, Jr. . |
| 3,124,771 | 3/1964 | Rohrback . |
| 3,436,713 | 4/1969 | Di Noia .................................. 338/28 |
| 3,939,873 | 2/1976 | Rinker et al. ............ 138/DIG. 7 X |
| 4,477,572 | 10/1984 | Anzenberger, Sr. . |
| 4,675,662 | 6/1987 | Kondo et al. ...................... 340/59 X |

Primary Examiner—Jerry W. Myracle
Attorney, Agent, or Firm—A. Mich, Jr.

[57] ABSTRACT

Disclosed is a method of measuring the depletion of basic additives in a lubricating oil. A sensor is immersed into the oil, an electric current is passed through the sensor, and the resistance of the sensor is measured. The sensor is made of copper, lead, mixtures of copper and lead, copper alloys, lead alloys, or mixtures thereof. Also disclosed is apparatus for indicating when the basic additives in a lubricating oil have been depleted. The apparatus consists of a sensor which is immersed in the oil, a first pair of electrodes for passing an electric current through the sensor, a second pair of electrodes for measuring the electrical resistance of the sensor, and an indicator for indicating when the electrical resistance has increased to a predetermined amount.

15 Claims, 4 Drawing Sheets

FIG. I

MEASUREMENT OF THE DEPLETION OF BASIC ADDITIVES IN LUBRICATING OIL

BACKGROUND OF THE INVENTION

Internal combustion engines require continuous lubrication for proper performance. As the lubricating oil in an engine oxidizes, however, it becomes acidic. The acidic oxidation products can attack various metals used in the bearings, bushings, connecting rods, pins, and other engine parts, and lead to failure of the engine. In order to prevent this from occurring, basic additives are mixed into most modern lubricating oils. The amount of basic additive that is present in the oil, and that is available for neutralizing the acids that form, is given by the total base number. A new lubricating oil might have a total base number of about 3 to about 15, but, as the basic additives become depleted, the total base number is lowered. Once the basic additives are completely depleted or reduced to a dangerously low level, the quantity of acid and corrosion oxidation products increases rapidly and the attack on the metal parts of the engine proceeds at a rapid pace. Most operators of large fleets of trucks test the total base number of the engine oil at periodic intervals. When the total base number has fallen to about 1 or 2, the oil is changed.

The total base number of the engine oil is determined by removing a sample of the engine oil and having the sample analyzed at an oil analysis laboratory. The disadvantage of this procedure is that there is usually a delay of one or two days between the time the sample is taken and the time that the analysis is returned to the maintenance shop. In the meantime, the truck is typically put back into service and may not be returned to the maintenance shop for an extended period of time. During that time, the basic additives could become further depleted, resulting in severe internal damage to the engine. The alternative of simply changing the engine oil at frequent intervals without performing the analysis is considered to be too expensive for diesel engines, which may contain 3 to 7 gallons of oil.

SUMMARY OF THE INVENTION

We have discovered that the depletion of basic additives in a lubricating oil can be accurately measured by immersing into the oil a sensor made of copper or lead, passing an electric current through the sensor, and measuring the electrical resistance of the sensor. We have found that as the total base number of the lubricating oil falls, the resistance of the sensor increases, but only if the sensor is made of copper or lead.

Our invention provides a continuous monitor of the total base number of the lubricating oil, so that when the total base number falls below a pre-selected level at which it is desirable to change the oil, an indicator light or other alarm can be turned on. As a result, the operator of the vehicle is warned immediately when the oil must be changed, but the oil is not changed more frequently than is necessary. The apparatus of this invention is relatively simple and inexpensive and can be installed on existing engines without extensive modification.

RELEVANT ART

U.S. Pat. No. 2,735,754 discloses measuring the corrosion of a metal by immersing a sensor into a medium in contact with the metal. The sensor is a strip of, for example, copper, and the resistance to passage of electricity through the strip is measured.

DESCRIPTION OF THE INVENTION

FIG. 4 shows how the resistance of the metals changes with time as the total base number of a lubricating oil decreases;

Figure 1:
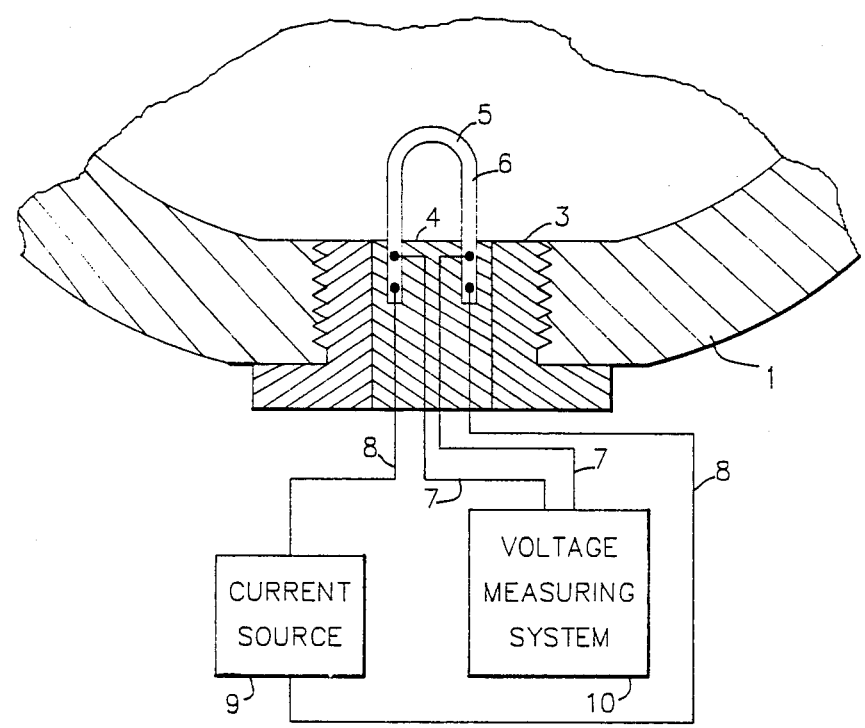
FIG. 1 is a side view in section illustrating a certain presently preferred embodiment of a sensor plug according to this invention, including the accompanying electric circuitry.

In FIG. 1, a sensor plug 1 according to this invention replaces the regular drain plug in bottom pan 2 of an internal combustion engine. The plug consists of a hollow metal screw 3 filled with a resinous material 4. Embedded in the resinous material is a U-shaped laminate 5 of, for example, glass reinforced epoxy, clad with a metal 6 of copper or lead. Attached to metal 6 are electrodes 7 and 8. A source of electric current 9 passes an electric current through electrodes 8 and metal foil 6. The voltage across the sensor is sensed by a voltmeter or other voltage measuring circuit 10 connected to terminals 7.

In the experiments hereinafter described, from which the data of FIGS. 4 and 5 resulted, the resistances of the sensors were rather low, as can be seen from the figures, of the order of a few hundredths of an ohm. Resistance values this low are difficult to measure accurately by a two-terminal measurement procedure, wherein the same connection terminals are used to pass a current through the sensor and to transmit the sensor voltage to the voltage measuring system, because the resistance of the connections and the wires to them will often be comparable to that of the sensor itself, and these connection resistances will also be included in the measurement and will be, improperly, attributed to the sensor. To avoid this problem, a four-terminal measurement procedure is used, wherein the sample (in this case the sensor) has two terminals at each end of its resistance; the current source is attached to one terminal at each end (terminals 8 in FIG. 1), and the voltage sensing system to the other two terminals (terminals 7). In this way, although connection resistances will still be present, they will not affect the determination of the sensor resistance, because voltage drops caused by the flow of the sensor current through the resistances of the current connections and leads will not be included in the voltage measured at the voltage terminals, and the voltage drops in the voltage terminal connections and leads will be negligible because the current flow in the voltage measuring system will be very small. The latter condition assumes the use of a voltmeter whose resistance is very high compared to that of the sensor, and this was the case in these experiments. The sensor resistance is then the voltage across the voltage terminals (here terminals 7) divided by the current through the current terminals (here terminals 8). For a constant current through the sensor, as it is progressively eroded and its resistance rises, the voltage across terminals 7 will also rise, and can be made to set off an alarm or other indicator when it has risen to a value corresponding to a prechosen oil acidity. The four-terminal arrangement shown in FIG. 1 is therefore preferred, although it is also possible to use only two terminals or some other arrangement.

While FIG. 1 illustrates a certain presently-preferred embodiment, other embodiments of the invention are also possible. In FIG. 1, the metal foil is supported by a laminate so that it will not be broken by turbulence in the oil. The foil can be wrapped or bonded to the laminate and other means of supporting the foil may also be used.

Figure 2:
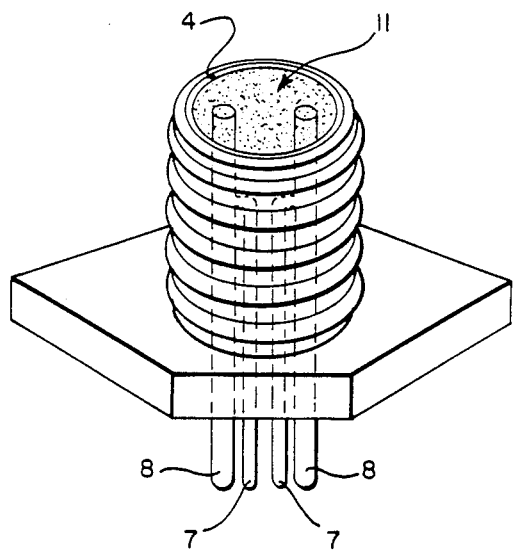
FIG. 2 is an isometric view of an alternative certain presently preferred embodiment of a sensor plug according to this invention.

FIG. 2, for example, shows an alternative embodiment of the apparatus of this invention. In FIG. 2 the sensor film 11 is deposited on the surface of the insulating resin 4 occupying the interior of the metallic screw plug in the oil pan drain opening. This film makes contact with wires 8, which may be flush with the resin surface or may extend somewhat beyond it into the oil. Separate voltage electrodes 7 for the lamp are connected to wires 8. It would alternatively also be possible to omit electrodes 7 and connect the lamp directly across electrodes 8. These two connective schemes respond somewhat differently to the occurrence of poor (that is, high-resistance) connections at the plug terminals.

Figure 3:
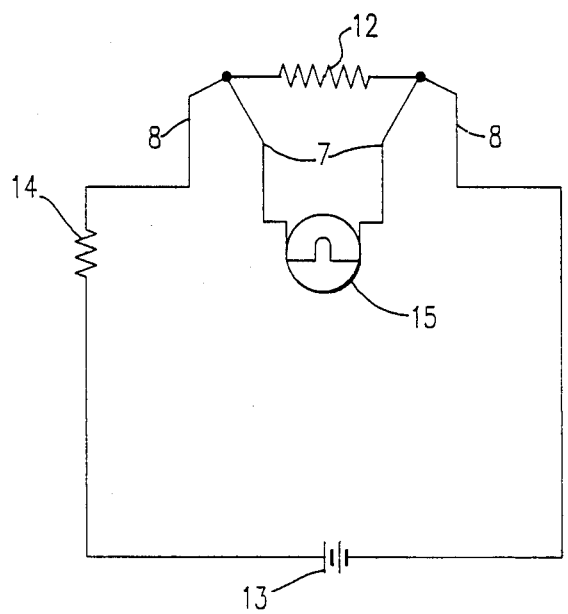
FIG. 3 is a side view showing electric circuitry for an indicator light in combination with a sensor according to this invention.

In laboratory measurements, or other cases, in which it is desired to observe quantitatively the progressive rise of sensor resistance with oil acidification, the techniques previously described for continuously monitoring the oil are recommended. For engine oil monitoring in the field, however, it may be simpler to have a system which will not continuously indicate the state of the oil but will merely provide an indication or alarm when the oil should be changed. A very simple system which does this is shown in FIG. 2. Here, the sensor's original film thickness is chosen so that it will erode completely through just when an oil change is required. That is, its original thickness is made to be just the amount which is observed to be eroded away by the time an oil change is necessary. In FIG. 3, the sensor film resistance 12, containing current terminals 8 and voltage terminals 7 (as previously described in reference to FIG. 1) is attached to a battery 13, which may be, for example, the main battery associated with the engine whose oil is being monitored, through a resistor 14. Voltage terminals 7 are connected to an indicator such as a light bulb 15. This bulb should reach full illumination at a voltage somewhat less than that of battery 13, and resistor 14 is chosen so that when the sensor film 11 is eroded entirely through and its resistance becomes infinite, the resulting current through bulb 15 will be its rated current. The sensor film in this case can be quite small in area and electrical length, and might typically have a resistance of the order of 0.01 ohms. If battery 13 is a 12-volt battery and bulb 15 is a 6-volt, 6-watt bulb (therefore of 6 ohms resistance when at 6 volts), resistor 14 would be a 6-ohm value. In its initial state, the voltage across the sensor would be very low; its current would be slightly less than 2 amperes, and the voltage across it and bulb 15 would be about 0.02 volt so that no visible illumination would occur. Even when 98% of the sensor's thickness has been eroded away, its resistance would have risen only to ½ ohm, and the bulb 15 would then have across it a voltage of less than 1 volt, which would not produce visible illumination. During the erosion of the last 2% of the sensor film's thickness, however, its resistance would rise from ½ ohm to infinity, and the voltage across the hub would rise from 1 to 6 volts, providing full illumination. Thus, closely enough, whenever illumination can be observed, it is time for an oil change. This is electrically a very simple and rugged system.

This invention is applicable to any lubricating oil that contains basic additives, including synthetic oils, mineral oils, and other types of lubricating oils. These additives are usually proprietary to the manufacturer of the lubricating oil, but the additives are typically compounds such as basic metal sulfonates, metal alkyl phenolates, or metal salts of acids of phosphorus. The amount and effectiveness of the basic additives that are present is given by the total base number. The total base number (TBN) is determined by titrating the lubricating oil with an acid. The formula is:

$$TBN = mg\ KOH/g = \frac{[(ml\ acid \times mormality) + (ml\ KOH \times normality)] \times 56.1}{gms\ of\ sample}$$

(The determination of the total base number is performed according to ASTM standards D664 and D974.)

Of a wide variety of metals tested for use in the sensor, including aluminum, zinc, iron, magnesium, lead, tin, and copper, we found that only lead and copper are useful. That is, only lead and copper corrode, and therefore increase in resistance, as the total base number of the lubricating oil falls. Also useful in the invention are mixtures of lead and copper, as well as lead alloys and copper alloys, and mixtures of lead and copper alloys. In order to maximize the sensitivity of the sensor metal, as much of the surface area as possible of the sensor should be exposed to the lubricating oil, and the metal should be not much thicker than is necessary to last until the basic additives have been depleted to the level at which it is desired to change the oil. The metal is preferably about 0.5 to about 2 mils thick as thinner metals may not last until the basic additives have been depleted and thicker metals will reduce the sensitivity of the sensor. The lubricating oil is preferably replaced whenever the total base number reaches a preselected level, but is is also possible to add additional basic additives to the oil. For most commercial fleet operators using diesel engines, the oil is replaced when the total base number reaches 1 or 2.

The sensor can be calibrated in the manner described in the Example which follows. Briefly, the sensor is immersed into a sample of the oil. The total base number of the oil is gradually lowered by, for example, adding oxidants or acid to the oil. Samples of the oil are then taken at the same time the resistance to an electric current through the sensor is measured. In this way, the relationship between the total base number of the oil and the progressive increase of the resistance of the sensor can be determined. A sensor of the same material and dimensions is then used in a similar electric circuit in a similar lubricating oil in the engine so that the sensor will respond in a similar manner. If it is desirable to change the oil in the engine at a total base number of, for example, 2, the oil in the engine is changed when the resistance of the engine sensor increases to the level which corresponded to a total base number of 2 in the calibration of the sample oil.

The following examples further illustrate this invention.

EXAMPLE

In a series of experiments, various metals were mounted in a plug similar to that shown in FIG. 1, and were immersed and tested in lubricating oils containing basic additives. Each metal specimen was two inches long and an eighth of an inch in width. The metals tested and their thicknesses were aluminum (1 mil), zinc (1 mil), iron (5 mils), magnesium (8 mils), lead (7 mils), tin (5 mils), and copper (1 mil).

Two oils were tested. The first oil was a synthetic oil sold by Mobil Oil Corporation under the trade designation "DELVAC No. 1." This oil contained a mixture of dibasic acid esters, linear alpha olefin oligimers, and proprietary basic additives. The total base number of this oil was 7. The second oil tested was a mineral oil sold by Mobil Oil Corporation under the trade designation "DELVAC Special 10W/30." This oil was a petroleum hydrocarbon oil containing a proprietary basic additive package. The total base number of this oil was 7.8.

Referring to FIG. 1, outside terminals 8 of the plug were connected to a source of current of 4.0 amps. The inner electrodes 7 were connected to a voltage-measuring system 10. Samples of the oil were taken periodically to determine the total base number of the oil, and the voltage to the voltmeter was noted when each sample was taken. By dividing the voltage at terminals 7 by the current in the circuit to electrodes 8, the resistance of the sensor was determined according to the formula: voltage divided by current equals resistance. The temperature of the oil in contact with the plug was maintained at 150° C.±1° C., and air was bubbled through the oil at a rate of 20 ml. a minute of oxidize the oil and deplete the basic additives.

Figure 4:
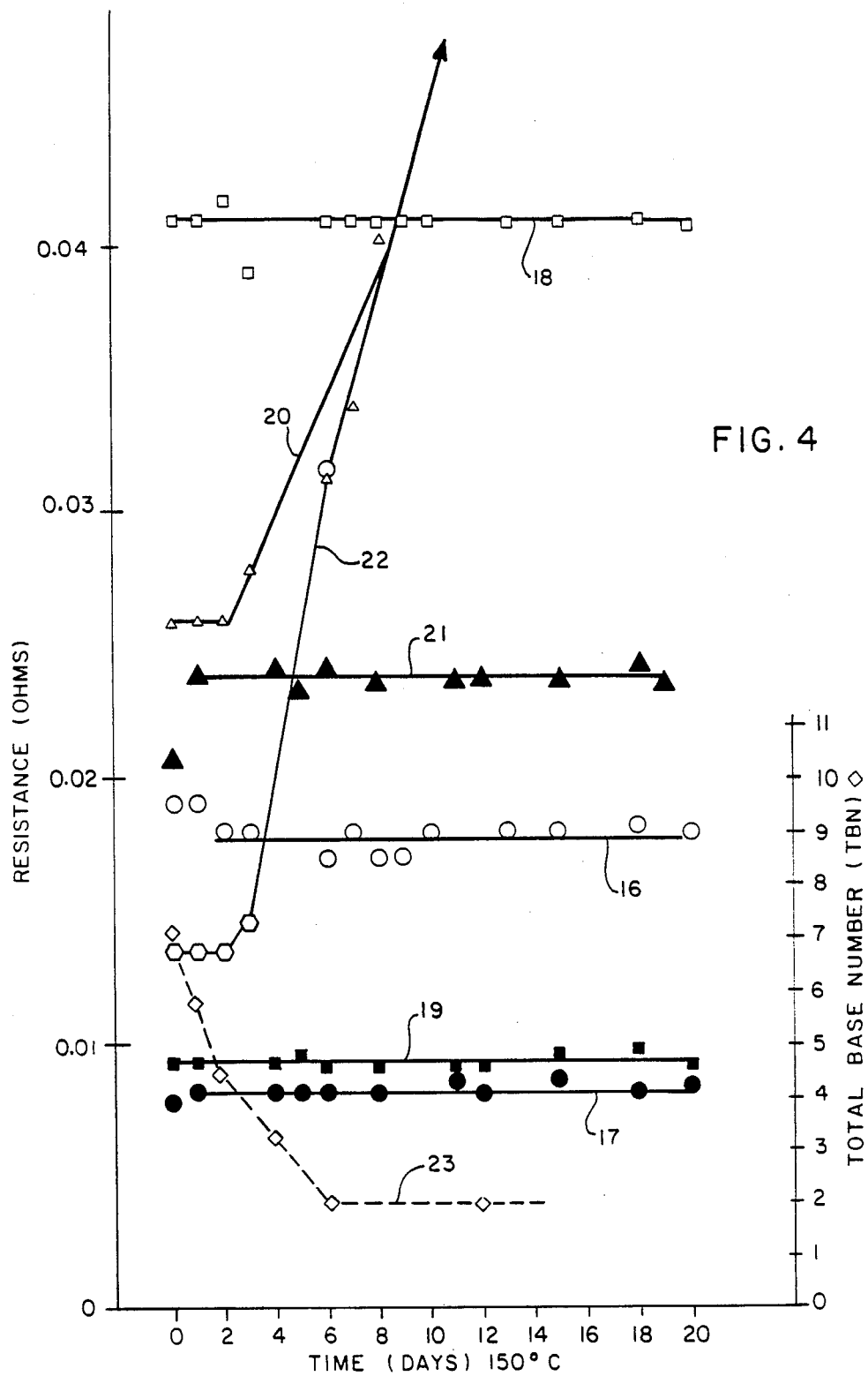
FIG. 4 is a graph which gives the results of experiments performed using various metals as sensors.
Figure 5:
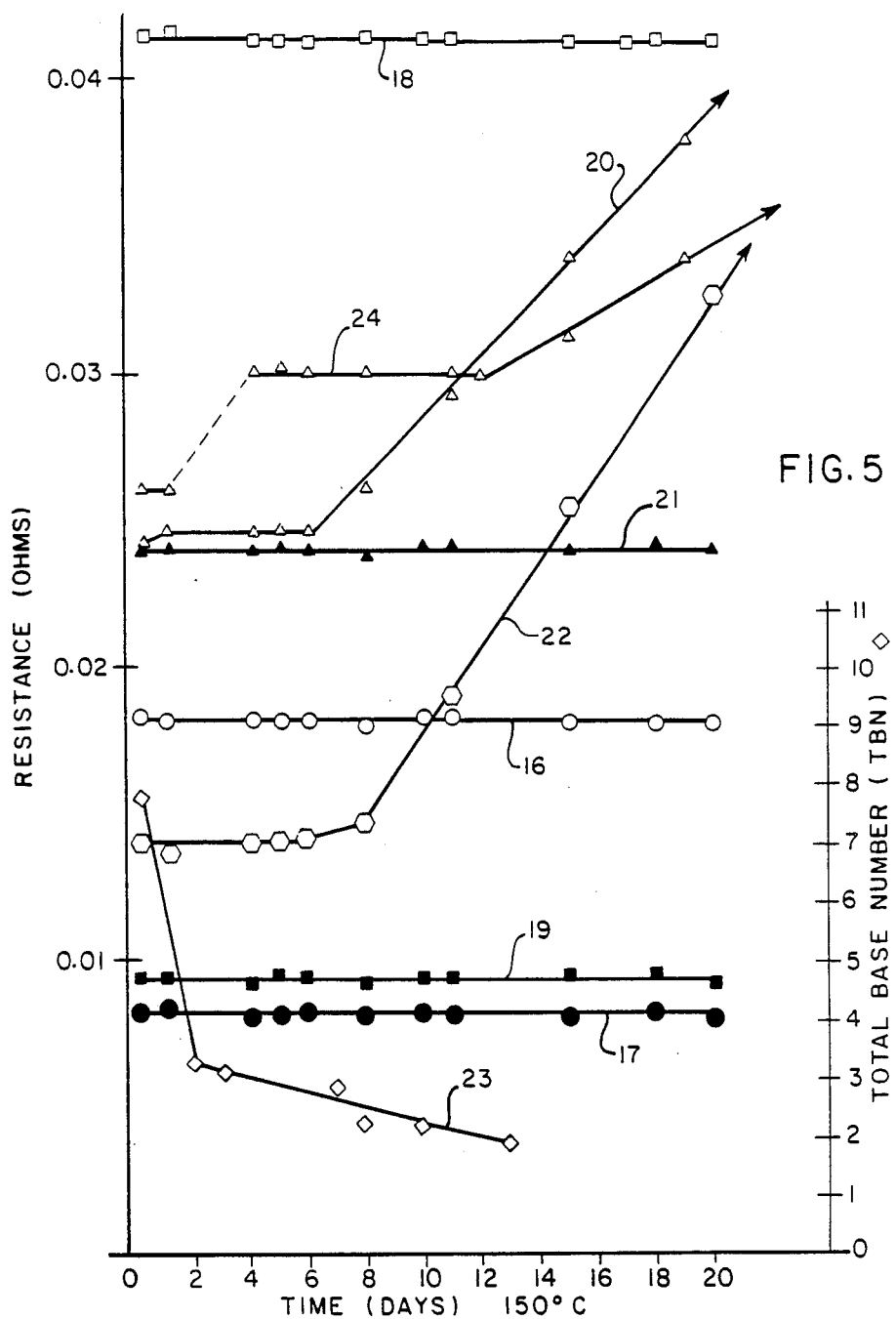
FIG. 5 is similar to FIG. 4, except that another type of lubricating oil was used.

FIG. 4 gives the results of the experiment using the synthetic oil, and FIG. 5 gives the results of testing in the mineral oil. In FIGS. 4 and 5, curve 16 is aluminum, curve 17 is zinc, curve 18 is iron, curve 19 is magnesium, curve 20 is lead, curve 21 is tin, curve 22 is copper, and curve 23 is the total base number. Also, in FIG. 5, curve 24 is lead in the presence of an air flow, of 20 ml/min., containing 1% by volume of $SO_2$. FIG. 4 shows that the total base number, curve 23, decreased from an initial value of 22 to a value of 2 after six days and was still at a value of 2 after 12 days. FIG. 4 also shows that of the seven metals tested, only copper and lead increased in resistance as the total base number declined, after an initial stable period of about three days. FIG. 5 shows that the total base number declined with time from an initial value of about 7.8 to a final value after 13 days of less than 2. FIG. 5 also shows that, of the seven metals tested, only copper and lead increased in resistance as the total base number declined. The results of these experiments indicate that only copper and lead are useful sensor materials for indicating depletion of basic additives in lubricating oils.

We claim:

1. A method of measuring the depletion of basic additives in a lubricating oil comprising:
   (A) immersing into said oil a sensor made of a metal consisting of lead;
   (B) passing an electric current through said sensor; and
   (C) measuring the electrical resistance of said sensor.

2. A method according to claim 1 including the initial first step of calibrating said sensor by samples of said sensor into samples of said oil and lowering the total base number of said oil while simultaneously measuring said total base number and the resistance to an electric current passed through said samples.

3. A method according to claim 1 wherein said resistance is measured over a sensor surface area exposed to said oil of about 0.1 to about 1 inch$^2$, and a sensor thickness of about 0.5 to about 2 mils.

4. A method according to claim 1 wherein said sensor is mounted on an insulating support.

5. A method according to claim 4 wherein said support is a laminate of glass reinforced epoxy.

6. A method according to claim 1 wherein said current is passed through said sensor by means of a first pair of electrodes attached to said sensor, and said resistance is measured by means of a second pair of electrodes also attached to said sensor.

7. A method according to claim 1 wherein said oil has a total base number of about 3 to about 15.

8. A method according to claim 1 wherein said oil is within a diesel engine.

9. A method according to claim 1 including the additional last step of turning on an indicator light when said resistance increases beyond a pre-selected amount.

10. In a diesel engine containing a lubricating oil which has a total base number of about 3 to about 15 due to the presence of basic additives in said oil, a method of indicating when the total base number of said oil has fallen to a replacement value, where it is desired to replace said oil in said engine, comprising:
    (A) immersing into a sample of said oil a sample strip of metal consisting of lead;
    (B) at the same time, measuring the total base number of said sample and the resistance to an electric current passed through said sample strip;
    (C) reducing the total base number of said sample, then repeating step (B) as many times as is necessary to obtain the resistance of said sample strip when said total base number of said sample is at said replacement value;
    (D) immersing a similar strip into said oil in said engine;
    (E) passing a similar electric current through said strip in said oil in said engine; and
    (F) when the resistance of said strip in said oil in said engine increases to the resistance of said sample strip at said replacement value, actuating an indicator which indicates that said replacement value has been reached.

11. In an internal combustion engine lubricated with an oil that contains basic additives, the improvement which comprises:
    (A) a sensor immersed in said oil, said sensor being made of a metal selected from the group consisting of lead;
    (B) means for passing an electric current through said sensor;
    (C) means for measuring the electrical resistance of said sensor; and
    (D) means for indicating when said electrical resistance has increased to a predetermined amount.

12. The improvement of claim 11 wherein said resistance is measured over a surface area of said sensor exposed to said oil of about 0.1 to about 1 inch$^2$, and said sensor has a thickness of about 0.5 to about 2 mils.

13. The improvement of claim 11 wherein said sensor is mounted on a laminate.

14. The improvement of claim 13 wherein said laminate is glass reinforced epoxy.

15. The improvement of claim 11 wherein said current is passed through said sensor by means of a first pair of electrodes, and said resistance is measured by means of a second pair of electrodes.

* * * * *